United States Patent
Kershman et al.

(10) Patent No.: US 11,484,483 B2
(45) Date of Patent: Nov. 1, 2022

(54) TOPICAL LOTION HAVING SANITIZING PROPERTIES

(71) Applicant: Shear Kershman Laboratories, Inc, Chesterfield, MO (US)

(72) Inventors: Alvin Kershman, Chesterfield, MO (US); Jeff Shear, Bonita Springs, FL (US); Doreen Linze, Labadie, MO (US); Linda L. Lewis, Pacific, MO (US)

(73) Assignee: Shear Kershman Laboratories, Inc., Chesterfield, MO (US)

( * ) Notice: Subject to any disclaimer, the term of this patent is extended or adjusted under 35 U.S.C. 154(b) by 0 days.

(21) Appl. No.: 17/361,230

(22) Filed: Jun. 28, 2021

(65) Prior Publication Data
US 2021/0401691 A1    Dec. 30, 2021

Related U.S. Application Data

(60) Provisional application No. 63/045,581, filed on Jun. 29, 2020.

(51) Int. Cl.

| | | |
|---|---|---|
| *A61Q 17/00* | (2006.01) | |
| *A61K 8/22* | (2006.01) | |
| *A61K 8/04* | (2006.01) | |
| *A61K 8/41* | (2006.01) | |
| *A61K 8/20* | (2006.01) | |
| *A61K 8/34* | (2006.01) | |
| *A61K 8/73* | (2006.01) | |
| *A61K 8/67* | (2006.01) | |
| *A61K 8/37* | (2006.01) | |
| *A61K 8/9789* | (2017.01) | |
| *A61K 8/36* | (2006.01) | |
| *A61K 8/92* | (2006.01) | |

(52) U.S. Cl.
CPC ................ *A61K 8/22* (2013.01); *A61K 8/042* (2013.01); *A61K 8/20* (2013.01); *A61K 8/345* (2013.01); *A61K 8/361* (2013.01); *A61K 8/375* (2013.01); *A61K 8/416* (2013.01); *A61K 8/678* (2013.01); *A61K 8/735* (2013.01); *A61K 8/92* (2013.01); *A61K 8/9789* (2017.08); *A61Q 17/005* (2013.01); *A61K 2800/48* (2013.01); *A61K 2800/49* (2013.01)

(58) Field of Classification Search
CPC .................. A61Q 17/005; A61K 8/416; A61K 2800/524; A61K 8/375; A61K 8/361; A61K 8/042; A61K 8/22; A61K 2800/51; A61K 8/92; A61K 2800/48; A61K 8/9789; A61K 8/20; A61K 8/345; A61K 8/735; A61K 2800/49
USPC ....................................................... 424/616
See application file for complete search history.

(56) References Cited

U.S. PATENT DOCUMENTS

| | | | | |
|---|---|---|---|---|
| 3,954,974 | A * | 5/1976 | Herzog ................... | A61K 33/40 424/616 |
| 6,383,505 | B1 * | 5/2002 | Kaiser .................... | A01N 47/44 424/407 |
| 8,048,620 | B2 * | 11/2011 | Ramirez-Arcos ...... | A61K 47/60 435/2 |
| 9,044,403 | B2 * | 6/2015 | Shultz .................... | A61K 8/927 |
| 9,173,941 | B1 * | 11/2015 | Shear ................. | A61K 31/5375 |
| 9,198,935 | B2 * | 12/2015 | Omidbakhsh ........ | A61Q 17/005 |
| 2019/0060213 | A1 * | 2/2019 | Revellame ............. | A61Q 19/10 |

* cited by examiner

*Primary Examiner* — Eisa B Elhilo
(74) *Attorney, Agent, or Firm* — Linda L. Lewis

(57) ABSTRACT

An alcohol-free lotion for the topical application having sanitizing properties is made by combining an aqueous phase comprising water, a water soluble preservative, an antimicrobial active, and at least one humectant with an oil phase, wherein the at least one humectant is present in the aqueous phase in the range of from 5 to 30 wt. %, wherein the oil phase comprises an oil soluble preservative, at least one surfactant, and at least one oil, wherein the surfactant is present in the oil phase in the range of from about 20 to 60 wt. %, and wherein the aqueous phase to oil phase ratio is from about 12:1 to 1:2.

20 Claims, No Drawings

TOPICAL LOTION HAVING SANITIZING PROPERTIES

CROSS-REFERENCE TO RELATED APPLICATIONS

This application claims the benefit of provisional patent application 63/045,581 filed Jun. 29, 2020 which is hereby incorporated by reference.

STATEMENT REGARDING FEDERALLY SPONSORED RESEARCH

Not Applicable.

APPENDIX

Not Applicable.

TECHNICAL FIELD

The present invention relates to a topical lotion having sanitizing and anti-viral properties.

BACKGROUND OF THE INVENTION

In the midst of a pandemic caused by the COVID-19, the most highly recommended way of preventing the transfer of the virus by physical contact is through handwashing using soap. It is explained that the COVID-19 is an enveloped virus which has a lipid exterior. Since soap is amphoteric, having a lipid portion of the molecule, and the soap attacks the virus exterior and breaks it up through handwashing.

Preventing the transfer of microbes through physical contact is not a new concept. U.S. Pat. No. 6,383,505 discloses an antimicrobial lotion for topical use having an oil-in-water emulsion with a dispersant of emollient droplets in an oil phase and an antimicrobial agent in a water phase. A combination of anionic and nonanionic surfactants stabilize the emulsion and maintain the cationic antimicrobial agent primarily in the water phase.

The World Health Organization published a homemade hand sanitizer of the following composition: isopropyl alcohol 75% (v/v), glycerol 1.45% (v/v) and hydrogen peroxide 0.125% (v/v). The repeated use of an alcohol-based hand sanitizer will have the undesirable effect of severely drying the skin of the user.

U.S. Pat. No. 3,954,974 discloses a disinfectant for the surface of human body parts, consisting essentially of an oil-in-water emulsion having a continuous aqueous phase containing an amount of hydrogen peroxide effective to disinfect human body parts upon contact, the oil phase being the dispersed phase of the emulsion and containing by weight, from 80 to 230 parts of glycerol monostearate, from 80 to 320 parts of paraffin oil, from 80 to 320 parts of cetyl alcohol, from 150 to 600 parts of petroleum jelly, and from 10 to 200 parts of a polyoxyethylene derivative of anhydrosorbitol partially esterified with a higher fatty acid.

U.S. Pat. No. 9,044,403 discloses a stable, sporicidal hand sanitizer formulation is described. The formulation is a lotion including peracetic acid, hydrogen peroxide, and one or more short chain alcohols. The lotion demonstrates an extended presence of active PAA and is capable of achieving a total kill of a bacteria in less than about 10 minutes contact time and more particularly, in about 2 minutes contact time.

U.S. Pat. No. 9,198,935 discloses an aqueous skin disinfecting solution having a pH of from about 2 to about 6, and consisting of at least (a) hydrogen peroxide in a concentration of from about 0.01 to about 4% w/w; (b) at least one surfactant chosen from alkyl betaines, alkyl amidopropyl betaines, alkyl amidopropyl betaine amides, alkylsulfobetaines, alkyl amphocarboxylates and amine oxides in a concentration of from about 0.01 to about 15% w/w; (c) at least one hydrogen peroxide stabilizer in a concentration of from about 0.01 to about 4% w/w; (d) at least one member chosen from cyclic carboxylic acids and salts thereof in a concentration of from about 0.01 to about 4% w/w; (e) at least one skin conditioning agent in a concentration of from about 0.01 to about 10% w/w; and (f) an effective amount of at least one solvent.

None of the above patents and references disclose the claimed invention.

The present invention is a topical lotion having sanitizing properties that has a continuous phase of oil enveloping the aqueous phase. Since it is known that lipids attack and destroy enveloped viruses, the present lotion is highly effective in destroying COVID-19. The continuous lipid phase also provides the lotion with hydrophobic properties which resists being washed off the skin. The lotion is observed as a thin layer on a slide under a microscope for visible cracking, pooling or pitting of the lotion surface. The ideal surface is smooth and glossy.

Further, the homogeneous hydrophobic lotion not only provides sanitizing properties on the skin, it also leaves an antimicrobial surface on the skin. This surface is resistant to being washed off, and is long lasting, for at least 4 or more hours. This antimicrobial surface kills microbes and prevents the transfer of bacteria or viruses by direct contact or indirect contact, from one surface to the next.

Since the COVID-19 infects the lungs via the nasal passages, the oral passages and the trachea, the delivery of the topical lotion to those areas via swabs, washes, atomizers, inhalers, sprays and aerosol sprays is also contemplated.

SUMMARY OF THE INVENTION

The present invention is a homogeneous topical lotion wherein the lotion contains from about 1.0 to 10 wt. % surfactant, from about 1.0 to 20.0 wt. % oil, from about 4.0 to 30.0 wt. % humectant, from about 0.01 to 5.0 wt. % gelling agent, from about 30 to 80 wt. % water, from about 1.0 to 3.0 oil soluble preservative, and from about 0.1 to 2.0 water soluble preservative. In a preferred embodiment, the lotion contains from about 0.1 to 10.0 wt. % antimicrobial agent and greater than about 0.125 wt. % hydrogen peroxide.

The present invention is made by combining an aqueous phase comprising water and at least one humectant with an oil phase to form a topical lotion with hydrophobic properties. The at least one humectant is present in the aqueous phase in the range of from about 5.0 to about 30.0 wt. %. In a preferred embodiment, the at least one humectant is present in the aqueous phase from about 7.0 to 25.0 wt. %. The oil phase comprises at least one surfactant and at least one oil. The surfactant is present in the oil phase in the range of from about 20 to 60 wt. %. In a preferred embodiment, the surfactant is present in the oil phase from about 25 to 55 wt. %. The aqueous phase is added to the oil phase in a weight ratio of about 12:1 to 1:2. The aqueous phase is added to the oil phase using low to medium shear mixing to provide the homogeneous hydrophobic topical lotion. The lotion is stable, hydrophobic, and has antiviral properties.

It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

The oil phase is prepared from a hydrophobic solution or mixture containing optionally at least one oil and/or petroleum distillate and at least one surfactant. The surfactant is preferably a non-water soluble surfactant having an HLB number of less than about 6, and includes emulsifiers. A preferred surfactant is commercially sold as ATMOS® 300K, and is a combination of mono- and di-glycerides made from edible food sources and propylene glycol with an HLB of 2.8. Another preferred surfactant is Defospum E100, a defoamer which is a combination of mono- and di-glycerides sold by Defotec. A third preferred surfactant is Lucrafoam E100, a defoamer which is a combination of mono-, di- and tri-glycerides sold by Levaco Chemicals.

In a preferred embodiment, the oil phase contains a second surfactant that has an HLB number of about 6. The preferred surfactant is glyceryl monostearate and has an HLB of about 5.8. In a more preferred embodiment, the ratio of ATMOS®300K surfactant to the glyceryl monostearate is from about 10:1 to about 1:1. In a preferred embodiment, the, ratio of ATMOS®300K surfactant to the glyceryl monostearate is from about 5:1 to about 1:1. The total surfactant is present in the oil phase in the amount of about 20 to 60 wt. %, and the oil is present in the oil phase from about 80 to 40 wt. %.

A third surfactant is benzylalkonium chloride, a water soluble cationic surfactant, which also provides antimicrobial properties. This surfactant is dissolved in the aqueous phase. Cationic surfactants cannot be used with anionic surfactants in this composition as the combination is unstable and often precipitates. The combination of three surfactants, e.g., ATMOS®300k, glyceryl monostearate and benzylaknomium chloride, is preferred.

Certain surfactants are not compatible with the present invention, and cause the lotion to fail, in that the continuous phase oil enveloping the aqueous phase either doesn't form or quickly breaks down. For example, the Tween surfactants, having a hydrophilic ethylene glycol head and hydrophobic alkyl tail, cause the lotion to fail. Tween 20 is a polysorbate monooleate nonionic surfactant that causes the lotion to break down into separate phases.

The oil suitable for the oil phase is typically liquid or semi-solid at room temperature, and is compatible with the topical applications. Such oils include essential oils, plant oils, such as vegetable oil, corn oil, canola oil, coconut oil, castor oil or olive oil, shea butter, and animal fats such as tallow and lard. The oils also include petroleum distillates, such as petrolatum and mineral oil. A preferred oil is mineral oil. Mixtures of oils are also contemplated in the present invention. The oil phase is present in the lotion in the range of from about 5 to 30 wt. %. In a preferred embodiment, the surfactant and the oil are present in the lotion in a weight ratio of about 1:4 to 1:1 surfactant to oil. Oils that act as emollients are also suitable for the present invention, and include vitamin E. In a preferred embodiment, the lotion contains from about 0.1 to 10.0 wt. % vitamin E.

Certain oils are not suitable for the present lotion. This includes castor oil, which has triglycerides having about 90% fatty acid chains from ricinoleats. Oleates and lioleates are other significant components.

Preferably, the lotion of the present invention has both an oil soluble preservative and a water soluble preservative. Preservatives are antimicrobial ingredients added to product formulations to maintain the microbiological safety of the products by inhibiting the growth of and reducing the amount of microbial contaminants. The antimicrobial preservatives include essential oils with germicidal properties. VegeCide® natural preservative is made from high purity sources of caprylic and undecylenic fatty acids. It contains glyceryl monocaprylate, and glyceryl monoundecylenate. It is oil soluble and considered useful when added to the oil phase of a product. Citricidal® preservative is water soluble preservative that is a grapefruit seed extract. It contains about 3 wt. % ascorbic acid, about 36 wt. % glycerol, and about 58.5 wt. % diphenol hydroxybenzene, a quaternary compound from a grapefruit bioflavinoid. Other preservatives include potassium sorbate. Antioxidants, such as ascorbic acid and Vitamin E may also be added to prevent oxidation and improve the shelf-life of the product.

Not all preservatives are compatible with the present invention. Alcohols such as methanol, ethanol, propanol, isopropanol, and butanol will cause the lotion to fail. Preservative alcohols such as benzyl alcohol and phenoxyethanol cause the lotion to separate into phases and fail. However, sugar alcohols, such as fructose and sorbitol, will not adversely affect the lotion.

The aqueous phase contains at least one humectant. Suitable humectants include, but are not limited to glycerin, lactic acid, polyols, propylene glycol, corn syrup, high fructose corn syrup (HFCS), including Cornsweet 55 (55 wt. % fructose, 24 wt. % water and 21 wt. % glucose) and Cornsweet 42 (42 wt. % fructose, 24. wt. % water and 34 wt. % glucose), and sorbitol. The at least one humectant is present in the aqueous phase from 2 to 86 wt. %. Preferably, the amount of humectant in the lotion is from about 5 to 50 wt. %. More preferably, the humectant is present from about 5 to 30 wt. %.

A preferred humectants is glycerin, which works to stabilize the lotion. More preferably the humectants in the lotion are from about 5 to 30 wt. % glycerol, and from about 1 to 10 wt. % sorbitol solution. A preferred sorbitol solution is non-crystalizing liquid sorbitol 70 wt. % in water.

Preferably, the aqueous phase also contains at least one antimicrobial as the active ingredient. Suitable antimicrobial agents include salts of chlorhexidine, such as chlorhexidene digluconate, chlorhexidene acetate, chlorhexidene isethionate, chlorhexidene hydrochloride. Other cationic antimicrobials may also be used, such as benzalkonium chloride (which also functions as a cationic surfactant), benzethonium chloride, polyhexamethylene biguanide, cetyl puridium chloride, methyl and benzothonium chloride. A preferred antimicrobial active is benzalkonium chloride, and a preferred concentration is from about 0.01 to about 0.3 wt. %.

Oxidative disinfectants share the property of acting as antimicrobial agents by oxidizing their proteins and cells. Such antimicrobial agents include hydrogen peroxide and hydrochlorous acid provide an antimicrobial effect which is desirable. Preferably, the hydrogen peroxide is present in the lotion from about 0.150 wt. % to 3.0 wt. %. More preferably, the hydrogen peroxide is present from greater than about 0.125 wt. % to 2.0 wt. %. Hydrochlorous acid, a source of hypochlorite ions and hydrogen ions, is present from about 0.010 to 0.100 wt. %.

A preferred combination of disinfectant and oxidative disinfectants provides both the desired short term (60 seconds) disinfecting and the desired long term (4 hour) disinfecting. This combination is benzylalkonium chloride and either hydrogen peroxide or hydrochlorous acid.

Various gelling agents can be employed including, for example and without limitation, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, the carbomers and carbopols, polyvinylpyrrolidone, polyethylene glycol, polyethylene oxide, polyvinyl alcohol, other polymeric materials, and mixtures thereof, etc. The pectin or pectic substances useful for this invention include not only purified or isolated pectates but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange. Preferred gelling agents are hyaluronic acid or its salt, carboxymethyl cellulose (CMC), guar gum, and a combination of guar gum and xanthan gum in the range of about 0.01 to 2.0 wt. %.

The claimed composition is typically prepared using a planetary or counter rotating type mixer having a rubber lined mixing bowl equipped with a wire whip stirring device. Preferably, the wire whip is rubber coated. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the lotion is conducted as follows:

Aqueous Phase:
1. Into a suitable container is measured the hyaluronic acid, sufficient water to make the desired concentration of hyaluronic acid mixture, and humectant (glycerin and/or sorbitol solution). The ingredients are mixed well.

Oil Phase:
1. Accurately weigh all oil phase ingredients (oil(s) and surfactant(s)) into the kitchen aid bowl.
2. Warm ingredients until homogeneously melted (10° F. above the highest melt point ingredient). Reduce the heat.

Mixing:
1. Keep the kitchen aid mixing on low speed and relatively low shear (30-600 rpm's) with the oil phase ingredients melted.
2. Add the active to the oil phase and mix about 1 minute.
3. Gradually, begin adding the Aqueous Phase ingredients to the bowl while continuing to mix at low speed while continuing to mix for 5 min after addition is complete.
4. Stop the mixer and scrap down the bowl and mixing blade.
5. Continuing mixing at speed 2 for an additional ten (10) minutes to produce the hydrophobic lotion.

The components of the hydrophobic lotion have the following preferred wt. % ranges:

Oil Phase:
Surfactant: 1.0-10.0
Oil: 1.0-20.0
Oil soluble Preservative: 1.0-3.0

Aqueous Phase:
Humectant: 4.0-30.0
Gelling agent: 0.01-5.0
Water: 30.0-80.0
Antimicrobial Agent: 0.01-10.0
Water soluble Preservative 0.1-2.0

In a preferred embodiment, the wt. % ranges for specific components are:

| | |
|---|---|
| ATMOS ® 300 | 1.0-25.0 |
| Glyceryl Stearate | 0.1-5.0 |
| Vitamin E | 0.1-10.0 |
| Citation 70 mineral oil | 2.0-26.0 |
| Vegecide ® Preservative | 1.0-3.0 |
| Glycerin | 4.0-30.0 |
| Hyaluronic Acid | 0.1-2.0 |
| Water | 5.0-80.0 |
| Benzalkonium Chloride | 0-10.0 |
| Citricide ® Preservative | 0.1-2.0 |
| Ascorbic Acid | 0-3.0 |
| Hydrogen Peroxide | 0-1.0 |
| Hydrochlorous acid | 0-0.10 |

In a second embodiment of the process of this invention, the lotion is prepared as a first step and a second step. The first step produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 12:1 to 1:2), this initial process step is concluded.

The second step begins with the seed batch of the first step, at the desired final weight ratio of aqueous phase to oil phase. The volume of seed material needed for the second step is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

Stability Testing

The lotion of the present invention is evaluated for stability by at least two (2) visual tests. In the first test, a small amount of lotion is spread in a thin layer on a microscope slide and observed periodically for about 24 hours. The layer is examined under a microscope at 10 to 40 times enlargement. It is examined for smoothness and glossiness, which indicates a successful formulation. If it is observed that the surface has cracking, pooling or pitting, then failure is determined. Also, signs of separating and the formation of two phases also indicates formulation failure.

For a second test, a cup is filled with deionized water and a portion of lotion is dropped into the water and submerges. The lotion is observed periodically for about 24 hour. A successful formulation for lotion expands (grows in size) due to absorbing water, intact, while submerged in the water. A failure includes lotion dissolving completely in the water, or floating on top of the water, or breaking into pieces which break when moved with spoonula.

Another test of the lotion is hand feel. The lotion should be non-greasy, non-drippy, yet smooth and silky feeling on the skin.

A sample was prepared in Control 1, below.

TABLE 1

Hydrophobic Topical Lotion Containing Benzalkonium Chloride
Control 1 0.23% BKC

| Ingredient | Weight | % |
|---|---|---|
| Oil Phase | | |
| ATMOS ® 300K- Surfactant | 5.9190 | 3.9460 |
| citation 70 - Mineral Oil | 8.2875 | 5.5250 |
| Vitamin E 1300IU (Natural Source) - Oil soluble vitamin | 1.1835 | 0.7890 |
| Glyceryl Stearate (GMS) - Surfactant | 2.3685 | 1.5790 |
| Aqueous Phase | | |
| Benzalkonium chloride solution - Active | 0.3480 | 0.2320 |
| Hyaluronic Acid Pure Powder - Gelling agent | 0.4128 | 0.2752 |
| purified water (Distilled) - for a 0.5 wt. % gelling mixture | 82.1517 | 54.7678 |
| Glycerin, USP 99.7% Excipient/ Food use - Humectant | 29.5980 | 19.7320 |
| purified water (Distilled) | 19.7310 | 13.1540 |
| Total | 150 | 100.00 |

Method of Preparing Hydrophobic Topical Lotion Containing Benzalkonium Chloride

A. Preparing the Aqueous Phase (88.2 wt. % of the Final Lotion)

1. Mix well all of the water, hyaluronic acid and glycerin.

B. Preparing Oil Phase (11.8 wt. % of Final Lotion)

1. Mix citation 70 mineral oil, ATMOS® 300K, vitamin E, and glyceryl monostearate.

2. Heat the mixture with stirring to 155° F. to form a homogeneous mixture. Reduce the heat to 130° F.

C. Forming the Lotion

1. Using a 5 quart lab Hobart type planetary lab/kitchen mixer with a rubber or plastic lined wire whip and rubber or plastic lined bowl add the oil phase and stir on #1 (low) setting.

2. Add the benzalkonium chloride to the oil phase and stir for about 1 min.

3. Slowly add the aqueous phase with mixing.

4. Continue mixing for 5 minutes, then scrape the sides of the bowl with a spatula to ensure thorough mixing.

5. Continue to mix for 10 minutes more on setting #2, making sure to scrape the sides of the bowl occasionally. After 10 minutes of mixing, the lotion is prepared.

The lotion of Control 1, Table 1, above, is a homogeneous hydrophobic lotion.

TABLE 2

Method of Preparing the Hydrophobic Topical Lotion Containing Benzalkonium Chloride
Control 2 0.26 BKC

| Ingredient | Weight | % |
|---|---|---|
| Oil Phase | | |
| Atmos 300K - Surfactant | 7.50 | 5.00 |
| citation 70 - Mineral Oil | 18.00 | 12.00 |
| Vitamin E 1300IU (Natural Source) - Oil soluble vitamin | 1.50 | 1.00 |
| Glyceryl Stearate (GMS) - Surfactant | 3.00 | 2.00 |
| Aqueous Phase | | |
| Benzalkonium chloride solution - Active | 0.39 | 0.26 |
| Hyaluronic Acid Pure Powder - Gelling agent | 0.7461 | 0.4974 |
| purified water (Distilled) - Water to make 1.0 wt. % mixture | 73.8639 | 49.2426 |
| Glycerin, USP 99.7% Excipient/ Food use - Humectant | 15.00 | 10.00 |
| purified water (Distilled) | 30.00 | 20.00 |
| Total | 150.0 | 100.00 |

A. Preparing the Aqueous Phase (80.0 wt. % of the Final Lotion)

1. Mix sufficient water and hyaluronic acid to make the indicated 1.0 wt. % mixture. Add the glycerin and mix well.

2. In a separate container, mix the benzalkonium chloride and the remainder of the water.

B. Preparing Oil Phase (20.0 wt. % of Final Lotion)

1. Mix the citation 70 mineral oil, ATMOS® 300K, vitamin E, and glyceryl monostearate.

2. Heat the mixture with stirring to 155° F. to form a homogeneous mixture. Reduce the heat to 130° F.

C. Forming the Lotion

1. Using a 5 quart lab Hobart type planetary lab/kitchen mixer with a rubber or plastic lined wire whip and rubber or plastic lined bowl add the oil phase and stir on #1 (low) setting.

2. Slowly, with continuous stirring, add the water/hyaluronic acid/glycerin mixture alternating with the benzalkonium chloride/water mixture until all the aqueous phase is added.

3. Continue mixing for 5 minutes, turn off the mixer, then scrape the sides of the bowl with a spatula to ensure thorough mixing.

4. Continue to mix for 10 minutes more on setting #2, making sure to scrape the sides of the bowl occasionally. After 10 minutes of mixing, the lotion is prepared.

The lotion of Control 2, Table 2, above, is a homogeneous hydrophobic lotion.

TABLE 3

Method of Preparing the Hydrophobic Topical Lotion Containing Chlorhexidine Digluconate
Control 3 2.0% Chlorhexidine digluconate

| Ingredient | Weight | % |
|---|---|---|
| Oil Phase | | |
| Atmos 300K - Surfactant | 3.7500 | 2.50 |
| citation 70 -mineral oil | 9.0000 | 6.00 |
| Vitamin E 1300IU (Natural Source) - oil soluble vitamin | 0.7500 | 0.50 |
| Glyceryl Stearate (GMS) - surfactant | 1.5000 | 1.00 |

TABLE 3-continued

Method of Preparing the Hydrophobic Topical Lotion
Containing Chlorhexidine Digluconate
Control 3 2.0% Chlorhexidine digluconate

| Ingredient | Weight | % |
|---|---|---|
| Aqueous Phase | | |
| Chlorhexidine Digluconate 20% Aqueous Solution( | 15.0000 | 10.00 (2.0 % chlorhexidine digluconate, 8.0 wt. % water |
| Hyaluronic Acid Pure Powder - gelling agent | 0.3563 | 0.2375 |
| purified water (Distilled) - to make a 0.5 wt. % hyaluronic acid mixture | 70.8938 | 47.2625 |
| Glycerin, USP 99.7% Excipient/Food use - humectant | 18.7500 | 12.50 |
| Sorbitol Solution 70% USP - humectant | 7.5000 | 5.00 (3.5 wt. % sorbitol, 1.5 wt. % water) |
| purified water (Distilled) | 22.5000 | 15.00 |
| Totals | 150 | 100.00 |

A. Preparing the Aqueous Phase (90.0 wt. % of the Final Lotion)

1. Mix sufficient water and hyaluronic acid to make the indicated 0.5 wt. % mixture. Add the glycerin and mix well.
2. In a separate container, mix the chlorhexidine digluconate and the remainder of the water.

B. Preparing Oil Phase (10.0 wt. % of Final Lotion)

1. Mix the citation 70 mineral oil, ATMOS® 300K, vitamin E, and glyceryl monostearate.
2. Heat the mixture with stirring to 155° F. to form a homogeneous mixture. Reduce the heat to 130° F.

C. Forming the Lotion

1. Using a 5 quart lab Hobart type planetary lab/kitchen mixer with a rubber or plastic lined wire whip and rubber or plastic lined bowl add the oil phase and stir on #1 (low) setting.
2. Slowly, with continuous stirring, add the water/hyaluronic acid/glycerin mixture alternating with the chlorhexidine digluconate/water mixture until all the aqueous phase is added.
3. Continue mixing for 5 minutes, turn off the mixer, and scrape the sides of the bowl with a spatula to ensure thorough mixing.
4. Continue to mix for 10 minutes more on setting #2, making sure to scrape the sides of the bowl occasionally. After 10 minutes of mixing, the lotion is prepared.

The lotion of Control 3, Table 3, above, is a homogeneous hydrophobic lotion.

TABLE 4

Method of Preparing the Hydrophobic Topical Lotion
Containing Chlorhexidine Digluconate and Benzalkonium Chloride
Control 4 - 0.1% BKC, 0.2% Chlorhexidine Digcluconate

| Ingredient | Weight | % |
|---|---|---|
| Oil Phase | | |
| Atmos 300K - Surfactant | 11.79 | 3.93% |
| citation 70 - Mineral oil | 16.50 | 5.50% |
| Vitamin E 1300IU (Natural Source) - Oil soluble vitamin | 2.40 | 0.80% |
| Glyceryl Stearate (GMS) - Surfactant | 4.65 | 1.55% |

TABLE 4-continued

Method of Preparing the Hydrophobic Topical Lotion
Containing Chlorhexidine Digluconate and Benzalkonium Chloride
Control 4 - 0.1% BKC, 0.2% Chlorhexidine Digcluconate

| Ingredient | Weight | % |
|---|---|---|
| Aqueous Phase | | |
| Benzalkonium chloride solution - Active | 0.30 | 0.10% |
| Chlorhexidine Digluconate 20% Aqueous Solution-Active | 3.00 | 1.00 (0.20 wt. % chlorhexidine digluconate, 0.80 wt. % water) |
| Hyaluronic Acid Pure Powder - gelling agent | 0.8076 | 0.2692% |
| purified water (Distilled) - water to make 0.5 wt. % mixture | 160.9524 | 53.6508% |
| Glycerin, USP 99.7% Excipient/Food use - humectant | 59.10 | 19.70% |
| purified water (Distilled) | 40.50 | 13.50% |
| Totals | 300 | 100.00% |

A. Preparing the Aqueous Phase (88.88 wt. % of the Final Lotion)

1. Mix sufficient water and hyaluronic acid to make the indicated 0.5 wt. % mixture. Add the glycerin and mix well.
2. In a separate container, mix the benzalkonium chloride and the chlorhexidine digluconate and the remainder of the water.

B. Preparing Oil Phase (11.12 wt. % of Final Lotion)

1. Mix the citation 70 mineral oil, ATMOS® 300K, vitamin E, and glyceryl monostearate.
2. Heat the mixture with stirring to 155° F. to form a homogeneous mixture. Reduce the heat to 130° F.

C. Forming the Lotion

1. Using a 5 quart lab Hobart type planetary lab/kitchen mixer with a rubber or plastic lined wire whip and rubber or plastic lined bowl add the oil phase and stir on #1 (low) setting.
2. Add the benzalkonium chloride to the mixture with stirring. Continue to stir for 1 minute.
3. Slowly, with continuous stirring, add the water/hyaluronic acid/glycerin mixture alternating with the chlorhexidine digluconate/water mixture until all the aqueous phase is added.
4. Continue mixing for 5 minutes, turn off the mixer, and scrape the sides of the bowl with a spatula to ensure thorough mixing.
5. Continue to mix for 10 minutes more on setting #2, making sure to scrape the sides of the bowl occasionally. After 10 minutes of mixing, the lotion is prepared.

The lotion of Control 4, Table 4, above, is a homogeneous hydrophobic lotion.

| Control 5 Castor Oil, 0.26% BKC | | |
|---|---|---|
| Ingredient | Weight | % |
| Oil Phase | | |
| Atmos 300K - Surfactant | 15.00 | 5.00% |
| Castor Oil, USP | 30.00 | 10.00% |
| Vegecide - Preservative | 6.00 | 2.00% |
| Vitamin E 1300IU (Natural Source) | 3.00 | 1.00% |
| Glyceryl Stearate-Surfactant | 6.00 | 2.00% |

Control 5 Castor Oil, 0.26% BKC

| Ingredient | Weight | % |
|---|---|---|
| Aqueous Phase | | |
| Benzalkonium chloride solution - Active | 0.78 | 0.26% |
| Hyaluronic Acid Pure Powder - Gelling agent | 1.4922 | 0.4974% |
| purified water (Distilled) | 147.7278 | 49.2426% |
| Glycerin, USP 99.7% Excipient/Food use - Humectant | 30.00 | 10.00% |
| purified water (Distilled) | 60.00 | 20.00% |

To prepare Control 5, the same procedure as for Control 3 was used. The product failed. It didn't gel and wasn't viscous enough. Additionally, it had an undesirable skin feel. Castor oil does not work for the present lotion.

Control 6 0.26% BKC

| Ingredient | Weight | % |
|---|---|---|
| Oil Phase | | |
| Atmos 300K | 13.50 | 4.50% |
| Vegecide | 7.50 | 2.50% |
| citation 70 | 30.00 | 10.00% |
| Vitamin E 1300IU (Natural Source) | 3.00 | 1.00% |
| Glyceryl Stearate (GMS) | 6.00 | 2.00% |
| Aqueous Phase | | |
| Benzalkonium chloride solution | 0.78 | 0.26% |
| Hyaluronic Acid Pure Powder | 1.50 | 0.50% |
| purified water (Distilled) | 192.72 | 64.24% |
| Glycerin, USP 99.7% Excipient/Food use | 30.00 | 10.00% |
| Sorbitol Solution 70% USP | 15.00 | 5.00% |

To prepare Control 6, the same procedure used for Control #3 was used. The product did not have a desirable hand feel.

Control 7 0.26% BKC

| Ingredient | Weight | % |
|---|---|---|
| Oil Phase | | |
| Atmos 300K | 15.00 | 5.00% |
| Vegecide | 6.00 | 2.00% |
| citation 70 | 30.00 | 10.00% |
| Vitamin E 1300IU (Natural Source) | 3.00 | 1.00% |
| Glyceryl Stearate (GMS) | 6.00 | 2.00% |
| Aqueous Phase | | |
| Benzalkonium chloride solution | 0.78 | 0.26% |
| Hyaluronic Acid Pure Powder | 1.4922 | 0.4974% |
| purified water (Distilled) | 147.7278 | 49.2426% |
| Glycerin, USP 99.7% Excipient/Food use | 30.00 | 10.00% |
| purified water (Distilled) | 60.00 | 20.00% |

Control 7 was prepared by the same procedure as used for Control 3. The formula was unstable.

Control 8 0.26% BKC

| Ingredient | Weight | % |
|---|---|---|
| Oil Phase | | |
| Atmos 300K | 15.00 | 5.00% |
| Vegecide | 6.00 | 2.00% |
| citation 70 | 31.50 | 10.50% |
| Vitamin E 1300IU (Natural Source) | 1.50 | 0.50% |
| Glyceryl Stearate (GMS) | 6.00 | 2.00% |
| Aqueous Phase | | |
| Benzalkonium chloride solution | 0.78 | 0.26% |
| Hyaluronic Acid Pure Powder | 1.6422 | 0.5474% |
| purified water (Distilled) | 162.5780 | 54.1926% |
| Glycerin, USP 99.7% Excipient/Food use | 16.50 | 5.50% |
| purified water (Distilled) | 45.00 | 15.00% |
| Ascorbic Acid 80 mesh | 7.5000 | 2.50% |
| Sorbitol Solution 70% USP | v6.0000 | 2.00% |

The formula for Control 8 was prepared by the method used to make of Control 3. This formula was unstable.

Control 9 0.26% BKC

| Ingredient | Weight | % |
|---|---|---|
| Oil Phase | | |
| Atmos 300K | 15.00 | 5.00% |
| Vegecide | 5.25 | 1.75% |
| citation 70 | 33.00 | 11.00% |
| Vitamin E 1300IU (Natural Source) | 1.50 | 0.50% |
| Glyceryl Stearate (GMS) | 5.25 | 1.75% |
| Aqueous Phase | | |
| Benzalkonium chloride solution | 0.78 | 0.26% |
| Hyaluronic Acid Pure Powder | 1.8672 | 0.6224% |
| purified water (Distilled) | 184.8528 | 61.6176% |
| Glycerin, USP 99.7% Excipient/Food use | 15.00 | 5.00% |
| purified water (Distilled) | 30.00 | 10.00% |
| Ascorbic Acid 80 mesh | 1.50 | 0.50% |
| Sorbitol Solution 70% USP | 6.00 | 2.00% |

Example 9 was prepared by the method used for Control 3. This formula was not viscous enough. It was too drippy.

Example 10 0.26% BKC
Oil soluble preservative and Water soluble preservative

| Ingredient | Weight | % |
|---|---|---|
| Oil Phase-step 1 | | |
| Atmos 300K | 15.00 | 5.00% |
| citation 70 | 32.22 | 10.74% |
| Vitamin E 1300IU (Natural Source) | 1.50 | 0.50% |
| Vegecide (Glyceryl Monocaprylate and Glyceryl Monoundecylenate) | 4.50 | 1.50% |
| Glyceryl Stearate (GMS) | 6.00 | 2.00% |
| Aqueous Phase | | |
| Set Aside | | |
| Benzalkonium chloride solution | 0.78 | 0.26% |
| CitricidaKD lliquid concentrate (Grapefruit seed extract) | 1.5000 | 0.50% |
| 24 h Mixture | | |
| Hyaluronic Acid Pure Powder | 2.175 | 0.725% |
| Ascorbic Acid 80 mesh | 2.175 | 0.725% |
| purified water (Distilled) | 213.15 | 71.05% |

-continued

| Example 10 0.26% BKC Oil soluble preservative and Water soluble preservative | | |
|---|---|---|
| Ingredient | Weight | % |
| Humectant Added to 24 h Mixture | | |
| Sorbitol Solution 70% USP | 6.00 | 2.00% |
| Glycerin, USP 99.7% Excipient/Food use | 15.00 | 5.00% |

Example 10 was prepared using the following method.

Aqueous Phase:

1. Mix together the water and Ascorbic Acid, and shake to dissolve completely. Add the Hyaluronic Acid and mix well. Refrigerate about 24 h.

2. After 24 h, mix the humectant aqueous phase ingredients, with the overnight water/hyaluronic acid/ascorbic acid mixture.

Oil Phase:

1. Weigh all oil phase into a mixing bowl.

2. Warm the mixture until homogeneously melted (10° F. above the highest melt point ingredient).

Mixing the Two Phases:

1. Keep the mixer on low speed (setting 1) with the melted oil phase mixture.

2. Add the water soluble preservative Grapefruit Seed Extract (Citricidal Preservative) and antimicrobial active/surfactant benzalkonium chloride, and mix for 1 minute.

3. Slowly begin adding the Aqueous Phase mixture to the mixing bowl while continuing to mix at low speed.

4. Continue adding until both phases combine to form one phase, taking care to scrape the bowl out, making sure all of the aqueous phase is mixed in.

5. Stop the mixer and scrape down the bowl and mixing blade.

6. Continuing mixing at speed 2 for an additional ten (10) to fifteen (15) minutes.

The lotion of Example 10 was stable, hydrophobic, and had good hand feel.

| Example 11 - Seabuckthorn 0.26% BKC | | |
|---|---|---|
| Ingredient | Weight | % |
| Oil Phase | | |
| Atmos 300K | 15.00 | 5.00% |
| citation 70 | 27.72 | 9.24% |
| Vitamin E 1300IU (Natural Source) | 1.50 | 0.50% |
| Glyceryl Stearate (GMS) | 6.00 | 2.00% |
| Vegecide | 3.00 | 1.00% |
| Seabuckthon Pulp CO2-to extract | 6.00 | 2.00% |
| Aqueous Phase Set Aside | | |
| Benzalkonium chloride solution | 0.78 | 0.26% |
| Citricidal ® liquid concentrate | 1.50 | 0.50% |
| Overnight Mixture | | |
| purified water (Distilled) | 211.41 | 70.47% |
| Ascorbic Acid 80 mesh | 1.545 | 0.515% |
| Hyaluronic Acid Pure Powder | 1.545 | 0.515% |
| Humectant added to Overnight Mixture | | |
| Glycerin, USP 99.7% Excipient/Food use | 24.00 | 8.00% |

Example 11 was prepared using the same procedure as used for Example 10. The lotion had a bright yellow color which was undesirable. The lotion has good skin feel.

| Example 12 - 0.26% BKC | | |
|---|---|---|
| Ingredient | Weight | % |
| Oil Phase | | |
| Atmos 300K (Surfactant) | 15.00 | 5.00% |
| Vegecide (65-99 wt. % glyceryl monocaprylate and 1-35 wt. % glyceryl monoundecylenate) | 4.50 | 1.50% |
| citation 70 (Mineral Oil) | 24.72 | 8.24% |
| Macadamia Nut Oil | 7.50 | 2.50% |
| Vitamin E 1300IU (Natural Source) | 1.50 | 0.50% |
| Glyceryl Stearate (GMS) (surfactant) | 6.00 | 2.00% |
| Aqueous phase Set Aside | | |
| Benzalkonium chloride solution (Germicide) | 0.78 | 0.26% |
| Citricidal ® liquid concentrate (Grapefruit seed extract) | 1.50 | 0.50% |
| Overnight Mixture | | |
| Hyaluronic Acid Pure Powder (Gelling agent) | 2.19 | 0.73% |
| purified water (Distilled) | 214.62 | 71.54% |
| Ascorbic Acid 80 mesh (Preservative) | 2.19 | 0.73% |
| Humectant added to Overnight Mixture | | |
| Sorbitol Solution 70% USP (Humectant) | 4.50 | 1.50% |
| Glycerin, USP 99.7% Excipient/Food use (Humectant) | 15.00 | 5.00% |

Example 12 was prepared according to the procedure of Example 10.

Testing the Germicidal Effectiveness of the Lotion, Example 10:

Tests 1 and 2, Four Canine Paws

These tests were made to determine efficacy of lotion in eliminating germs from being carried by dog's paws and transferred into the home. Each of the four canine paws will be swabbed using 3M sponge stick with buffered peptone water broth swabs. There are multiple swabs of each paw, and a fresh sponge stick is used each time. The sponge sticks are cultured in broth and analyzed for Total Plate Count.

Process:

1. All four paws were swabbed for the initial swabs. (1st set of swabs)

2. Lotion formulae were applied using a soft sponge paint brush, taking care to cover entire paw from the tip of the nail, under the nails, all pads, webbing (top and bottom) and up to the dew claw area. The paws were not swabbed for about 10 minutes. The paws were swabbed a second time. (2nd set of swabs)

4. The dog will then maintained normal activities, going outside, running, eating, drinking, etc.

5. At about 4-6 hours after applying the lotion, all four paws were swabbed. The dog did not go outside for 20-30 minutes prior to this sample point. (3rd set of swabs)

6. Dog again maintained normal activities and final swabs were performed at 24 hours post lotion application. The dog did not go outside for 20-30 minutes prior to this sample point. (4th and final set of swabs)

Swabbing Directions:

Bottom of paws were swabbed carefully taking care to cover all areas of the paw. The swab sponge was turned over and swabbing repeated prior to carefully inserting into the individual bag provided with each sponge stick. All the used sponge sticks were immediately refrigerated for storage until shipped to the lab for analysis.

Gloves were worn and great care was taken while handling swabs to ensure no contamination occurred during sampling and transferring the sample into the provided bags. Carefully break the sticks off while the sponge is in the bag and dispose of it. Carefully close the bag, fold it down and twist the blue tabs until secure.

Test 1 Results

The same lotion was applied to all paws.

Bacteria count in broth.

| Sample | Paw | Pre-Application of Lotion | 0.5 h | 5 h | 24 h |
|---|---|---|---|---|---|
| Control #2 | Left Front | 1,800 | 980 | 1300 | 2,400 |
| Control #2 | Right Front | 2,200 | 820 | 880 | 150 |
| Control #2 | Right Rear | 2,700 | 2,200 | 550 | 540 |
| Control #2 | Left Rear | 1,900 | 1,100 | 7,500 | 4,100 |

There was no clear-cut overall reduction in bacteria count, although there was some drop in bacterial count after 0.5 h, it was not the sanitizing effect desired. It was noted that it was a rainy day and the dog repeatedly went outside to the wet and muddy yard.

Test 2 Results:

Three different lotions were applied, one to each paw. The fourth paw was untreated.

Samples:

Example 10 was applied to the Left Front Paw—0.13 wt. % BKC

Control 2 was applied to the Right Front Paw—0.13 wt. % BKC

Blank—The Left Rear Paw will be UNTREATED

Control 3 was applied to the Right Rear Paw—2% CHG formula

The Bacteria Count:

| Sample | Paw | Pre Treatment | 0.167 h | 5 h | 5.75 h | 24 h |
|---|---|---|---|---|---|---|
| Ex-10 | LF | 7,100 | 240 | 10 | 2,300 | 3,200 |
| C-2 | RF | 1,400 | 6,200 | 1,000 | 130,000 | 21,000 |
| C-3 | RR | 4,000 | 2,700 | 2,300 | 150,000 | 37,000 |
| Untreated | LR | 2,700 | 30,000 | 3,600,000 | X | 46,000 |

With Example 10, there was an immediate and dramatic drop in bacteria, which was increased at 5 h. Even at 5.75 h and 24 h, there was a reduction in bacteria compared to the pre-treatment value. With Controls 2 and 3, there was no dramatic reduction in bacteria, and at 5.75 h and 24 h there was a dramatic increase.

Test 3

One hand each was treated with Germ-X® or with the lotion prepared in Example 10. The same procedure as used for Tests 1 and 2 was used, except that human hands were treated with lotion or Germ-X® and then swabbed.

Germ-X® is a composition having 62% ethyl alcohol. It also contains water, glycerin, acrylates/C10-30 alkyl acrylate crosspolymer, propylene glycol and triethanolamine. It is a widely known and accepted hand sanitizer. The sanitizing agent in Germ-X is ethyl alcohol. The present invention does not contain ethyl or isopropyl alcohol.

| Sample | Hand | Pre Treatment | 0.033 h | 0.167 h | 1 h | 8 h |
|---|---|---|---|---|---|---|
| Germ-X® Hand sanitizer | Right | 6900 | 20* | 140 | 260 | 40* |

| Sample | Hand | Pre Treatment | 0.033 h | 0.167 h | 1 h | 8 h |
|---|---|---|---|---|---|---|
| 74-19 Ex. 10 | Left | 1,800 | <10 | 130 | 10* | <10 |

The results of Example 10 show dramatic sanitizing of the left hand. Additionally, the sanitizing effect is long-lasting for up to 8 h.

It is desirable for a sanitizing lotion to provide a sanitizing effect within 60 seconds. It is more preferable to have a sanitizing lotion to provide a sanitizing effect within 60 seconds and to provide long term effectiveness for at least 4 hours. The following samples using a variety of antimicrobial agents were prepared to provide those two effects.

| Control 13 (PLACEBO) No Antimicrobial | | |
|---|---|---|
| Ingredient | Weight | % |
| Oil Phase | | |
| Atmos 300K | 25.00 | 5.00% |
| citation 70 | 52.50 | 10.50% |
| Vegecide | 7.50 | 1.50% |
| Vitamin E 1300IU (Natural Source) | 2.50 | 0.50% |
| Aqueous Phase Set Aside | | |
| Glyceryl Stearate (GMS) | 10.00 | 2.00% |
| GRAPEFRUIT SEED EXTRACT (GSE) | 2.50 | 0.50% |
| 24 Hour Mix | | |
| Hyaluronic Acid Pure Powder | 2.50 | 0.50% |
| purified water (Distilled) | 362.50 | 72.50% |
| Humectant added to 24 Hour Mix | | |
| Sorbitol Solution 70% USP | 10.00 | 2.00% |
| Glycerin, USP 99.7% Excipient/Food use | 25.00 | 5.00% |

A placebo (Control 13) was prepared that did not contain any antimicrobial agents (not including preservatives as antimicrobial agents) using the same procedure as Example 10.

| Example 14 Zinc Sulfate and BKC | | |
|---|---|---|
| Ingredient | Weight | % |
| Oil Phase | | |
| Atmos 300K | 15.00 | 5.00% |
| Benzalkonium Chloride (50% in Water) | 0.39 | 0.13% |
| GRAPEFRUIT SEED EXTRACT (GSE) | 1.50 | 0.50% |
| Vitamin E 1300IU (Natural Source) | 1.50 | 0.50% |
| citation 70 | 31.11 | 10.37% |
| Aqueous Phase Set Aside | | |
| Glyceryl Stearate (GMS) | 6.00 | 2.00% |
| Vegecide | 4.50 | 1.50% |

Example 14 Zinc Sulfate and BKC

| Ingredient | Weight | % |
|---|---|---|
| 24 h. Mix | | |
| Hyaluronic Acid Pure Powder | 1.50 | 0.50% |
| purified water (Distilled) | 196.50 | 65.50% |
| Add to 24 h. Mix | | |
| Glycerin, USP 99.7% Excipient/Food use | 21.00 | 7.00% |
| Sorbitol Solution 70% USP | 6.00 | 2.00% |
| Zinc Sulfate Monohydrate (antimicrobial agent) | 15.00 | 5.00% |

Control 14 was prepared using zinc sulfate and benzalkonium chloride as antimicrobial agents.

Control 15 - Ethanol and BKC

| Ingredient | Weight | % |
|---|---|---|
| Oil Phase | | |
| LucraFoam E100 (Surfactant) | 15.00 | 5.00% |
| citation 70 | 31.101 | 10.367% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous phase Set aside | | |
| GRAPEFRUIT SEED EXTRACT (GSE) | 1.50 | 0.50% |
| Benzalkonium Chloride 95% | 0.399 | 0.133% |
| 24. h Mix | | |
| Everclear or Ethanol, 200 Proof | 30.00 | 10.00% |
| Hyaluronic Acid Pure Powder | 1.50 | 0.50% |
| purified water (Distilled) | 181.50 | 60.50% |
| Add to 24 h. Mix | | |
| Sorbitol Solution 70% USP | 6.00 | 2.00% |
| Glycerin, USP 99.7% Excipient/Food use | 21.00 | 7.00% |

Control 15 used 10% ethanol and benzalkonium chloride as antimicrobial agents. The oil-soluble surfactant Lucrafoam was used in place of Atmos 300.

Control 16 - Isopropyl Alcohol and BKC

| Ingredient | Weight | % |
|---|---|---|
| Oil Phase | | |
| Atmos 300K | 15.00 | 5.00% |
| citation 70 | 31.10 | 10.37% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous Phase Set aside | | |
| GRAPEFRUIT SEED EXTRACT (GSE) | 1.50 | 0.50% |
| Benzalkonium Chloride 95% | 0.40 | 0.13% |
| 24 h. Mix | | |
| Isopropyl Alcohol 99% | 30.00 | 10.00% |
| Hyaluronic Acid Pure Powder | 1.50 | 0.50% |
| purified water (Distilled) | 148.50 | 49.50% |
| Glycerin, USP 99.7% Excipient/Food use | 21.00 | 7.00% |

Control 16 - Isopropyl Alcohol and BKC

| Ingredient | Weight | % |
|---|---|---|
| Add to 24 h. Mix | | |
| Sorbitol Solution 70% USP | 6.00 | 2.00% |
| purified water (Distilled) | 33.00 | 11.00% |

Control 16 used 10% isopropyl alcohol and benzalkonium chloride as antimicrobial agents.

Control 17 used 70 wt. % isopropyl alcohol, neat.

Example 18 - 0.13 BKC

| Ingredient | Weight | % |
|---|---|---|
| Oil Phase | | |
| Atmos 300K | 15.00 | 5.00% |
| citation 70 | 32.00 | 10.67% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous Phase Set Aside | | |
| Benzalkonium Chloride 95% | 0.40 | 0.13% |
| GRAPEFRUIT SEED EXTRACT (GSE) | 0.60 | 0.20% |
| 24 h. Mix | | |
| Hyaluronic Acid Pure Powder | 1.50 | 0.50% |
| purified water (Distilled) | 211.50 | 70.50% |
| Add to 24 h. Mix | | |
| Sorbitol Solution 70% USP | 6.00 | 2.00% |
| Glycerin, USP 99.7% Excipient/Food use | 21.00 | 7.00% |

Example 18 used benzalkonium chloride as an antimicrobial agent.

Example 19 0.13% BKC and 0.69% $H_2O_2$

| Ingredient | Weight | % |
|---|---|---|
| Oil Phase | | |
| Atmos 300K | 15.00 | 5.00% |
| citation 70 | 31.101 | 10.367% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous phase Set aside | | |
| Benzalkonium Chloride 95% | 0.399 | 0.133% |
| GRAPEFRUIT SEED EXTRACT (GSE) | 1.50 | 0.50% |
| 24 h. Mix | | |
| Hyaluronic Acid Pure Powder | 1.50 | 0.50% |
| Hydrogen Peroxide 3% | 69.00 | 23.00% (0.69% $H_2O_2$, 22.31% water) |
| purified water (Distilled) | 148.50 | 49.50% |
| Add to 24 h. Mix | | |
| Sorbitol Solution 70% USP | 6.00 | 2.00% |
| Glycerin, USP 99.7% Excipient/Food use | 15.00 | 5.00% |

Example 19 used hydrogen peroxide and benzalkonium chloride as antimicrobial agents.

| Example 20 0.13% BKC/1.5 H$_2$O$_2$% | | |
|---|---|---|
| Ingredient | Weight | % |
| Oil Phase | | |
| Atmos 300K | 15.00 | 5.00% |
| citation 70 | 27.72 | 9.24% |
| Macadamia Nut Oil | 7.50 | 2.50% |
| Vitamin E 1300IU (Natural Source) | 1.50 | 0.50% |
| Glyceryl Stearate (GMS) | 6.00 | 2.00% |
| Aqueous Phase | | |
| Set aside | | |
| Benzalkonium chloride solution | 0.78 | 0.26% |
| GRAPEFRUIT SEED EXTRACT (GSE) | 1.50 | 0.50% |
| 24 h. Mix | | |
| Hyaluronic Acid Pure Powder | 0.69 | 0.23% |
| Hydrogen Peroxide 3% | 150.00 | 50.00% (1.5% H2O2, 48.5% water) |
| purified water (Distilled) Add to 24 h. Mix | 68.31 | 22.77% |
| Sorbitol Solution 70% USP | 6.00 | 2.00% |
| Glycerin, USP 99.7% Excipient/Food use | 15.00 | 5.00% |

Example 20 used hydrogen peroxide and benzalkonium chloride as antimicrobial agents.

| Control 21 0.13% BKC/0.125% H$_2$O$_2$ | | |
|---|---|---|
| Ingredient | Weight | % |
| Oil Phase | | |
| Atmos 300K | 15.00 | 5.00% |
| citation 70 | 31.101 | 10.367% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous Phase | | |
| Set Aside | | |
| Benzalkonium Chloride 95% | 0.399 | 0.133% |
| GRAPEFRUIT SEED EXTRACT (GSE) | 1.50 | 0.50% |
| 24 h. Mix | | |
| Hyaluronic Acid Pure Powder | 1.50 | 0.50% |
| Hydrogen Peroxide 3% | 12.51 | 4.17% |
| purified water (Distilled) Add to 24 h. Mix | 204.99 | 68.33% |
| Sorbitol Solution 70% USP | 6.00 | 2.00% |
| Glycerin, USP 99.7% Excipient/Food use | 15.00 | 5.00% |

Control 21 used hydrogen peroxide and benzalkonium chloride as antimicrobial agents, but the amount of hydrogen peroxide was too low.

| Control 22 Ethanol and BKC | | |
|---|---|---|
| Ingredient | Weight | % |
| Oil Phase | | |
| LucraFoam E100 (Surfactant) | 15.00 | 5.00% |
| citation 70 | 31.101 | 10.367% |
| Vegecide | 4.50 | 1.50% |
| Vitamin E 1300IU (Natural Source) | 1.50 | 0.50% |
| Glyceryl Stearate (GMS) | 6.00 | 2.00% |
| Aqueous Phase | | |
| Set Aside | | |
| GRAPEFRUIT SEED EXTRACT (GSE) | 1.50 | 0.50% |
| Benzalkonium Chloride 95% | 0.399 | 0.133% |
| 24 h. Mix | | |
| Ethanol 200 Proof Alcohol | 30.00 | 10.00% |
| Hyaluronic Acid Pure Powder | 1.50 | 0.50% |
| purified water (Distilled) Add to 24 h. Mix | 181.50 | 60.50% |
| Sorbitol Solution 70% USP | 6.00 | 2.00% |
| Glycerin, USP 99.7% Excipient/Food use | 21.00 | 7.00% |

Control 22 used ethanol and benzalkonium chloride as antimicrobial agents.

| Example 23 Hydrochlorous Acid and BKC | | | | |
|---|---|---|---|---|
| RM # | Ingredient | Weight | % | |
| 720 | Atmos 300K | 15.00 | 5.00% | |
| 445 | citation 70 | 31.101 | 10.367% | |
| 1558 | Vegecide | 4.50 | 1.50% | |
| 992 | Vitamin E 1300IU (Natural Source) | 1.50 | 0.50% | |
| 1555 | Glyceryl Stearate (GMS) | 6.00 | 2.00% | |
| 1758 | Benzalkonium Chloride 95% | 0.399 | 0.133% | |
| 1706 | GRAPEFRUIT SEED EXTRACT (GSE) | 1.50 | 0.50% | |
| 1508 | Hyaluronic Acid Pure Powder | 1.50 | 0.50% | |
| 1793 | Hypochlorous acid aqueous solution 0.05 wt. % | 150.00 | 50.00% (0.025% HOCl, 49.975% water) | |
| 997 | Sorbitol Solution 70% USP | 12.00 | 4.00% | |
| 995 | Glycerin, USP 99.7% Excipient/Food use | 24.00 | 8.00% | |
| 529 | purified water (Distilled) | 52.50 | 17.50% | |

Example 23 used hypochlorous acid and BKC.

| Example 24-Hydrochlorous acid | | |
|---|---|---|
| Ingredient | Weight | % |
| Atmos 300K | 15.00 | 5.00% |
| citation 70 | 30.75 | 10.25% |
| Vegecide | 4.50 | 1.50% |
| Vitamin E 1300IU (Natural Source) | 1.50 | 0.50% |
| Glyceryl Stearate (GMS) | 6.00 | 2.00% |
| GRAPEFRUIT SEED EXTRACT (GSE) | 2.25 | 0.75% |
| Hyaluronic Acid Pure Powder | 1.50 | 0.50% |
| Hydrochlorous acid aqueous solution 0.05% | 150.00 | 50.00% 0.(025% HOCl, 49.975% water) |

-continued

| Example 24-Hydrochlorous acid | | |
|---|---|---|
| Ingredient | Weight | % |
| Sorbitol Solution 70% USP | 12.00 | 4.00% |
| Glycerin, USP 99.7% | 28.50 | 9.50% |
| Excipient/Food use purified water (Distilled) | 48.00 | 16.00% |

Example 24 used hydrochlorous acid.

Efficacy Study of *E. coli* Strain 25922

On a coupon, 0.05 mL of the inocula (*E. coli* strain 25922) was added to the center of each test coupon and left to dry. Using a sterile glove, 0.05 grams of the test lotion was mechanically rubbed onto the test coupon to mimic rubbing hand sanitizer onto the skin of hands. There was a contact time of either 60 seconds or 4 hours allowed to lapse prior to placing the coupon touch transfer to the trypticase soy agar (TSA) plate. The coupon was then placed onto the TSA plate and allowed contact for 15 seconds in 3 different locations. The plates were then incubated for 24 hours at 37° C.

| Formula-Test Interval | Rep | Placement 1/*CFU | Placement 2/*CFU | Placement 3/*CFU | Organisms per coupon | Log Reduction |
|---|---|---|---|---|---|---|
| C-13-No sanitizer- Placebo - 60 s | 1 | **TNTC | **TNTC | **TNTC | $2.5 \times 10^6$ | 0 |
|  | 2 | **TNTC | **TNTC | **TNTC |  | 0 |
| E-14, .13% BKC, 5% $ZnSO_4$ - 60 s | 1 | **TNTC | **TNTC | 4 | $2.5 \times 10^6$ | 0-5.6 |
|  | 2 | **TNTC | 2 | 1 |  | 0-6 |
| C-15, .133% BKC, 10% EthOH - 60 s | 1 | 1 | 0 | 0 | $2.5 \times 10^6$ | 6 |
|  | 2 | 0 | 0 | 0 |  | 6 |
| C-16, .13% BKC, 10% IPA - 60 s | 1 | 1 | 0 | 0 | $2.5 \times 10^6$ | 6 |
|  | 2 | 0 | 0 | 0 |  | 6 |
| Control-70% IPA 60 s | 1 | 0 | 0 | 0 | $4.4 \times 10^4$ | 6 |
|  | 2 | 0 | 0 | 0 |  | 6 |
| E-18, .13% BKC - 60 s | 1 | **TNTC | **TNTC | **TNTC | $4.4 \times 10^4$ | 0 |
|  | 2 | **TNTC | **TNTC | **TNTC |  | 0 |
| E-18, .13% BKC - 4 h | 1 | 0 | 0 | 0 | $4.4 \times 10^4$ | 6 |
|  | 2 | 0 | 0 | 0 |  | 6 |
| E-19, .133 BKC, .69% $H_2O_2$ - 60 s | 1 | 0 | 0 | 0 | $2.5 \times 10^6$ | 6 |
|  | 2 | 0 | 0 | 0 |  | 6 |
| E-19, .133 BKC, .69% $H_2O_2$ - 4 h | 1 | 0 | 0 | 0 | $4.9 \times 10^5$ | 6 |
|  | 2 | 0 | 0 | 0 |  | 6 |
| E-20, .26 BKC, 1.5% $H_2O_2$ - 60 s | 1 | 0 | 0 | 0 | $2.5 \times 10^6$ | 6 |
|  | 2 | 0 | 0 | 0 |  | 6 |
| E-20, .26 BKC, 1.5% $H_2O_2$ - 4 h | 1 | 0 | 0 | 0 | $4.9 \times 10^5$ | 6 |
|  | 2 | 0 | 0 | 0 |  | 6 |
| E-21, .133 BKC, .125% $H_2O_2$ - 60 s | 1 | **TNTC | **TNTC | **TNTC | $4.4 \times 10^4$ | 0 |
|  | 2 | **TNTC | **TNTC | **TNTC |  | 0 |
| E-21, .133 BKC, .125% $H_2O_2$ - 60 s | 1 | 0 | 0 | 0 | $4.4 \times 10^4$ | 6 |
|  | 2 | 0 | 0 | 0 |  | 6 |
| C-22 10% EtOH - 60 s | 1 | **TNTC | **TNTC | **TNTC | $4.4 \times 10^4$ | 0 |
|  | 2 | **TNTC | **TNTC | **TNTC |  | 0 |
| C-22 10% EtOH - 60 s | 1 | 2 | 1 | 1 | $4.4 \times 10^4$ | 4.2 |
|  | 1 | 0 | 0 | 1 |  | 4.4 |
| E-23 0.13% BKC, 0.025% Hydrochlorous Acid 60 s | 1 | 0 | 0 | 0 | $3.6 \times 10^5$ | 6 |
|  | 2 | 0 | 0 | 0 |  | 6 |
| E-24 0.025% Hydrochlorous Acid 60 s | 1 | 0 | 0 | 0 | $3.6 \times 10^5$ | 6 |
|  | 2 | 2 | 1 | 1 |  | 4 |

*Colony Forming Units

**Too Numerous to Count

Criteria - ~5 Log Reduction in 60 sec.

The samples containing sufficient hydrogen peroxide and BKC (Examples 19 and 30) gave the desired performance at both 60 s. and 4 h. Sample E-23 with hdyrochlorous acid and BKC also gave the desired performance at 60 seconds. Examples E-18 and E-21 (BKC and BKC with low level of hydrogen peroxide) performed well at 4 hours. Alcohol containing control samples (Control 15, 16 and 22) gave inconsistent performance and the lotions were not stable and tended to deteriorate.

These embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A lotion for topical application to the skin having sanitizing properties made by the process of combining:
    A) an aqueous phase comprising water, at least one humectant, and at least one water soluble preservative;
       wherein the at least one humectant is present in the aqueous phase in the range of from about 5 to 30 wt. %;
    B) an oil phase comprising at least one surfactant, at least one oil, and at least one oil soluble preservative;
       wherein the at least one surfactant is present in the oil phase in the range of from about 20 to 60 wt. %;
       wherein the at least one surfactant comprises mono- and di-glycerides made from edible food sources and propylene glycol with an HLB of less than about 6; and
    c) at least one antimicrobial active;
       wherein the aqueous phase is added to the oil phase in a weight ratio of about 12:1 to 1:2,
       and the aqueous phase is added to oil phase using low to medium shear mixing to provide the lotion;
       wherein the lotion does not contain polysorbate monooleate nonionic surfactants;
       wherein the lotion is hydrophobic;
       wherein the lotion is alcohol free, and
       wherein the lotion has sanitizing properties.

2. The lotion of claim 1, wherein the aqueous phase further comprises a gelling agent.

3. The lotion of claim 1, wherein the at least one surfactant further comprises glyceryl monostearate;
    wherein the ratio of mono- and di-glycerides made from edible food sources and propylene glycol with an HLB of less than 6 to the glyceryl monostearate is from about 5:1 to about 1:1;
    wherein the total surfactant is present in the oil phase in the amount of about 20 to 60 wt. %; and
    wherein the oil is present in the oil phase from about 80 to 40 wt. %.

4. The lotion of claim 3, wherein the at least one antimicrobial active is selected from the group consisting of benzylalkonium chloride, hydrogen peroxide, and hydrochlorous acid.

5. The lotion of claim 4, wherein the water soluble preservative comprises a grapefruit seed extract.

6. The lotion of claim 5, wherein the oil soluble preservative comprises caprylic and undecylenic fatty acids.

7. The lotion of claim 6, wherein the at least one antimicrobial active comprises a cationic surfactant, and wherein the lotion does not contain an anionic surfactant.

8. A lotion for topical application to the skin having sanitizing properties made by the process of:
    adding a gelling agent to the water, shaking, and cooling to form a viscous aqueous solution;
    after about 12 h, mixing at least one humectant with the viscous aqueous solution;
    wherein the at least one humectant is present in the viscous aqueous solution in the range of from about 5 to 30 wt. %;
    adding to a mixing container at least one oil, at least one surfactant, and an oil soluble preservative to form an oil mixture;
    wherein the at least one surfactant is present in the oil mixture in the range of from about 20 to 60 wt.%;
    warming the oil mixture until melted forming a warm oil mixture;
    mixing the warm oil mixture using low shear mixing;
    adding to the warm oil mixture a water soluble preservative and an antimicrobial active and mixing for about one minute;
    slowly adding the viscous aqueous solution mixture to the mixing container while continuing to mix with low to medium shear mixing; and
    continue mixing until both the warm oil mixture and the viscous aqueous solution combine to form one phase;
    wherein the one phase is an alcohol-free lotion having sanitizing properties;
    wherein the at least one surfactant comprises glyceryl monostearate, and mono- and di-glycerides made from edible food sources and propylene glycol with an HLB of less than 6;
    wherein the ratio of mono- and di-glycerides made from edible food sources and propylene glycol with an HLB of less than 6 to the glyceryl monostearate is from about 5:1 to about 1:1;
    wherein the total surfactant is present in the oil phase in the amount of about 20 to 60 wt. %;
    wherein the oil is present in the oil phase from about 80 to 40 wt. %; and
    wherein the lotion does not contain polysorbate monooleate nonionic surfactants.

9. The lotion of claim 8, wherein the gelling agent comprises hyaluronic acid.

10. The lotion of claim 9, wherein the at least one surfactant is selected from the group consisting of monoglycerides, diglycerides, triglycerides, and combinations thereof.

11. The lotion of claim 10, wherein the at least one antimicrobial active is selected from the group consisting of benzylalkonium chloride, hydrogen peroxide, and hydrochlorous acid and combinations thereof; and wherein the lotion does not contain an anionic surfactant.

12. The lotion of claim 11, wherein the water soluble preservative comprises a grapefruit seed extract.

13. The lotion of claim 12, wherein the oil soluble preservative comprises caprylic and undecylenic fatty acids.

14. The lotion of claim 13, wherein the hydrogen peroxide is added to the aqueous phase in the amount of greater than 0.125 wt. % of the lotion.

15. A lotion for topical application to the skin having sanitizing properties comprising:

| Component | Wt. % |
|---|---|
| Surfactant: | 1.0-10.0 |
| Oil: | 1.0-20.0 |
| Oil soluble Preservative: | 1.0-3.0 |
| Humectant: | 4.0-30.0 |
| Gelling agent: | 0.01-5.0 |
| Water: | 30.0-80.0 |
| Antimicrobial Agent: | 0.01-10.0 |
| Water soluble Preservative | 0.1-2.0 | wherein the at least one surfactant comprises glyceryl monostearate and mono- and di-glycerides made from edible food sources and propylene glycol with an HLB of less than 6;

wherein the ratio of mono- and di-glycerides made from edible food sources and propylene glycol with an HLB of less than 6 to the glyceryl monostearate is from about 5:1 to about 1:1;

wherein the total surfactant is present in the oil phase in the amount of about 20 to 60 wt. %;

wherein the oil is present in the oil phase from about 80 to 40 wt. %;

wherein the lotion does not contain polysorbate monooleate nonionic surfactants;

wherein the lotion is homogeneous and hydrophobic;

wherein the lotion is alcohol free; and wherein when topically applied provides skin with germicidal properties.

16. The lotion of claim 15, wherein the at least one antimicrobial active comprises a cationic surfactant, and wherein the lotion does not contain an anionic surfactant.

17. The method of claim 16, wherein the at least one antimicrobial active is selected from the group consisting of benzylalkonium chloride, hydrogen peroxide, and hydrochlorous acid and combinations thereof.

18. The lotion of claim 17, wherein the at least one humectant is selected from the group consisting of glycerine, lactic acid, polyols, propylene glycol, high fructose corn syrup, and sorbitol and combinations thereof.

19. The lotion of claim 18, wherein the gelling agent is selected from the group consisting of hyaluronic acid, the salt of hyaluronic acid, carboxymethyl cellulose, guar gum, and a combination of guar gum and xanthan gum.

20. The lotion of claim 19, wherein the water soluble preservative comprises a grapefruit seed extract; and wherein the oil soluble preservative comprises caprylic and undecylenic fatty acids.

* * * * *